(12) United States Patent
Birikh et al.

(10) Patent No.: US 9,840,726 B2
(45) Date of Patent: Dec. 12, 2017

(54) METHOD FOR IMPROVING THE FERMENTABLE SUGAR YIELD FROM LIGNOCELLULOSIC

(71) Applicant: METGEN OY, Kaarina (FI)

(72) Inventors: Klara Birikh, Kaarina (FI); Alexey Azhayev, Kaarina (FI)

(73) Assignee: METGEN OY, Kaarina (FI)

( * ) Notice: Subject to any disclaimer, the term of this patent is extended or adjusted under 35 U.S.C. 154(b) by 0 days.

(21) Appl. No.: 14/778,545

(22) PCT Filed: Mar. 20, 2013

(86) PCT No.: PCT/EP2013/055867
§ 371 (c)(1),
(2) Date: Sep. 18, 2015

(87) PCT Pub. No.: WO2014/146713
PCT Pub. Date: Sep. 25, 2014

(65) Prior Publication Data
US 2016/0060664 A1    Mar. 3, 2016

(51) Int. Cl.
| | | |
|---|---|---|
| *C12N 9/26* | (2006.01) | |
| *C12P 19/02* | (2006.01) | |
| *C12P 19/14* | (2006.01) | |
| *C12N 9/02* | (2006.01) | |
| *C13K 1/02* | (2006.01) | |

(52) U.S. Cl.
CPC ............ *C12P 19/14* (2013.01); *C12N 9/0061* (2013.01); *C12P 19/02* (2013.01); *C12Y 110/03002* (2013.01); *C13K 1/02* (2013.01); *C12P 2203/00* (2013.01); *Y02P 20/52* (2015.11)

(58) Field of Classification Search
CPC .......... C12N 9/02; C12N 9/2425; D21C 5/00; C12P 2203/00; C12P 2201/00
See application file for complete search history.

(56) References Cited

U.S. PATENT DOCUMENTS

| | | | |
|---|---|---|---|
| 2010/0268000 A1* | 10/2010 | Parekh | C12P 7/065 568/840 |
| 2015/0159144 A1* | 6/2015 | Birikh | C12N 9/0061 435/189 |

FOREIGN PATENT DOCUMENTS

| | | |
|---|---|---|
| CN | 101463367 | 11/2006 |
| CN | 102154150 | 11/2010 |
| WO | 2013038062 | 3/2013 |
| WO | 2014146713 | 9/2014 |

OTHER PUBLICATIONS

Moilanen et al., The laccase-catalyzed modification of lignin for enzymatic hydrolysis, Enzyme and Microbial Technology, 2011, pp. 492-498, vol. 49.
Michine, Metgen—The Art of Biocatalysis, Company presentation material, 2013, pp. 1-15, Retrieved from the Internet: URL:http://events.cleantech.com/munich/sites/default/files/MetGen_Presentation_Cleantech_Forum_Europe.pdf [retrieved on Nov. 28, 2013].
Database WPI, Thomson Scientific, London, GB; An 2009-L05538 XP002717145, Jun. 24, 2009.
PCT International Search Report dated Dec. 17, 2013, PCT/EP2013/055867.
PCT International Preliminary Report on Patentability for PCT/EP2013/055867 dated Sep. 22, 2015.
Furtado et al., A designed bifunctional laccase/beta-I, 3-I, 4-glucanase enzyme shows synergistic sugar release from milled sugarcane bagasse, Protein Engineering, Design & Selection, 2013, vol. 26, No. 1, pp. 15-23.
European Patent Office, Communication pursuant to Article 94(3), dated Jun. 29, 2016, 2 pages.
European Patent Office, Form 2906 for Application No. 13 710 440.2 dated Jun. 29, 2016, 3 pages.
Definition of reducing sugar from Oxford Dictionaries available at https://en.oxforddictionaries.com/definition/reducing_sugar, visited Jul. 24, 2017.

* cited by examiner

*Primary Examiner* — Maryam Monshipouri
(74) *Attorney, Agent, or Firm* — TraskBritt, P.C.

(57) ABSTRACT

The invention relates to processes for the conversion of biomass into carbohydrates, notable fermentable sugars. It provides means and methods for increasing the yield of enzymatic digestion of a biomass, in particular in those cases where cellulose is converted into sugars using a cellulose converting enzyme. More in particular, the invention relates to a method for producing a fermentable sugar from a lignocellulosic material wherein the lignocellulosic material is contacted with a laccase and an enzyme capable of degrading cellulose, either simultaneously or in a sequentially deferred fashion, wherein the laccase is the *Bacillus* spore coat protein CotA.

10 Claims, 1 Drawing Sheet

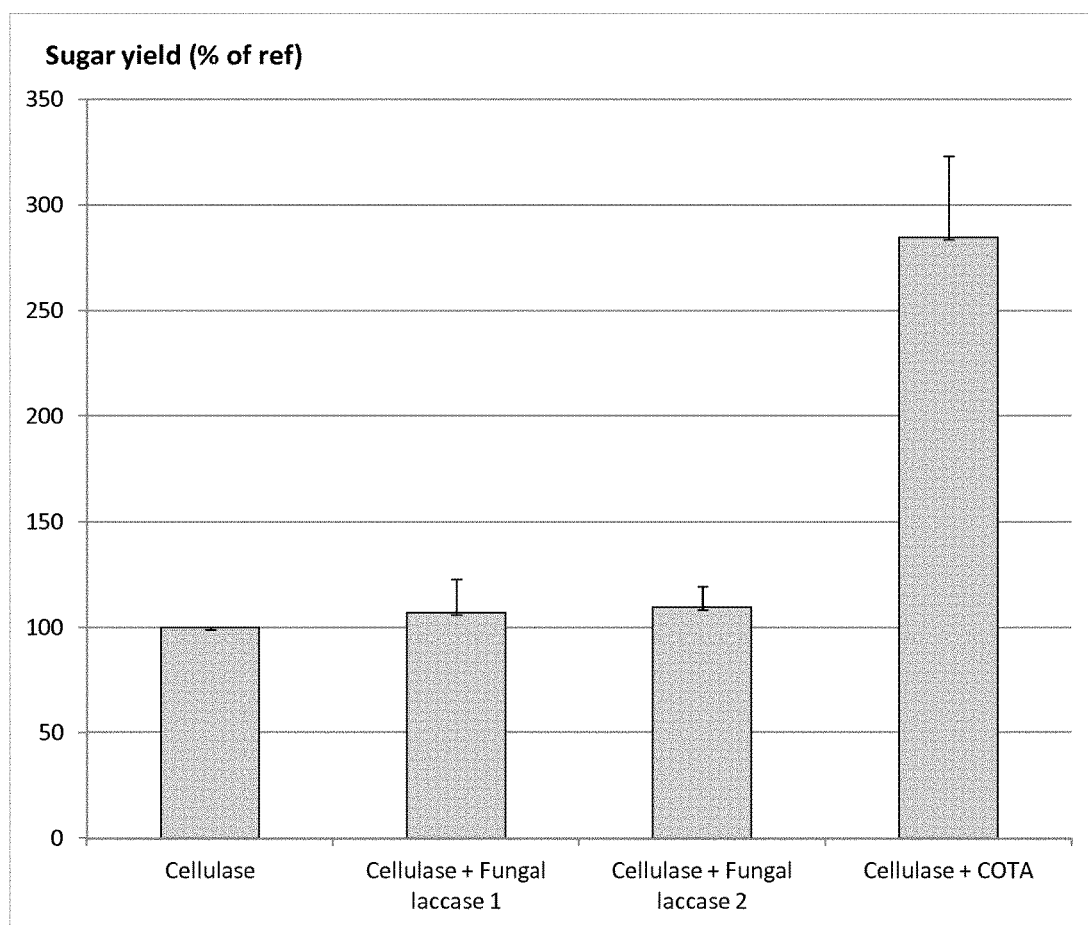

SEQUENCE LISTING

<160> NUMBER OF SEQ ID NOS: 2

<210> SEQ ID NO 1
<211> LENGTH: 513
<212> TYPE: PRT
<213> ORGANISM: Bacillus subtilis

<400> SEQUENCE: 1

Met Thr Leu Glu Lys Phe Val Asp Ala Leu Pro Ile Pro Asp Thr Leu
1               5                   10                  15

-continued

Lys Pro Val Gln Gln Thr Thr Glu Lys Thr Tyr Tyr Glu Val Thr Met
            20                  25                  30

Glu Glu Cys Ala His Gln Leu His Arg Asp Leu Pro Pro Thr Arg Leu
            35                  40                  45

Trp Gly Tyr Asn Gly Leu Phe Pro Gly Pro Thr Ile Glu Val Lys Arg
 50                  55                  60

Asn Glu Asn Val Tyr Val Lys Trp Met Asn Asn Leu Pro Ser Glu His
65                   70                  75                  80

Phe Leu Pro Ile Asp His Thr Ile His His Ser Asp Ser Gln His Glu
                85                  90                  95

Glu Pro Glu Val Lys Thr Val Val His Leu His Gly Gly Val Thr Pro
            100                 105                 110

Asp Asp Ser Asp Gly Tyr Pro Glu Ala Trp Phe Ser Lys Asp Phe Glu
            115                 120                 125

Gln Thr Gly Pro Tyr Phe Lys Arg Glu Val Tyr His Tyr Pro Asn Gln
    130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Asp Tyr Ile Ile His Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Glu Asp Gly Ser Leu Phe Tyr
            195                 200                 205

Pro Ser Gly Pro Glu Asn Pro Ser Pro Ser Leu Pro Lys Pro Ser Ile
            210                 215                 220

Val Pro Ala Phe Cys Gly Asp Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Glu
            260                 265                 270

Phe Ile Gln Ile Gly Ser Asp Gly Gly Leu Leu Pro Arg Ser Val Lys
            275                 280                 285

Leu Asn Ser Phe Ser Leu Ala Pro Ala Glu Arg Tyr Asp Ile Ile Ile
290                 295                 300

Asp Phe Thr Ala Tyr Glu Gly Glu Ser Ile Ile Leu Ala Asn Ser Glu
305                 310                 315                 320

Gly Cys Gly Gly Asp Ala Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile Gln Asn
            355                 360                 365

Ile Arg Thr Leu Lys Leu Ala Gly Thr Gln Asp Glu Tyr Gly Arg Pro
            370                 375                 380

Val Leu Leu Leu Asn Asn Lys Arg Trp His Asp Pro Val Thr Glu Ala
385                 390                 395                 400

Pro Lys Ala Gly Thr Thr Glu Ile Trp Ser Ile Val Asn Pro Thr Gln
                405                 410                 415

Gly Thr His Pro Ile His Leu His Leu Val Ser Phe Arg Val Leu Asp
            420                 425                 430

-continued

Arg Arg Pro Phe Asp Ile Ala Arg Tyr Gln Glu Arg Gly Glu Leu Ser
        435                 440                 445

Tyr Thr Gly Pro Ala Val Pro Pro Pro Ser Glu Lys Gly Trp Lys
450                     455                 460

Asp Thr Ile Gln Ala His Ala Gly Glu Val Leu Arg Ile Ala Val Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510

Lys

<210> SEQ ID NO 2
<211> LENGTH: 539
<212> TYPE: PRT
<213> ORGANISM: Bacillus subtilis

<400> SEQUENCE: 2

Met Thr Leu Glu Lys Phe Val Asp Ala Leu Pro Ile Pro Asp Thr Leu
1               5                   10                  15

Lys Pro Val Gln Gln Ser Lys Gly Lys Thr Tyr Tyr Glu Val Thr Met
            20                  25                  30

Glu Glu Cys Thr His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Thr His
65                  70                  75                  80

Phe Leu Pro Ile Asp His Thr Ile His His Ser Asp Ser Gln His Glu
                85                  90                  95

Glu Pro Glu Val Lys Thr Val Val His Leu His Gly Gly Val Thr Pro
            100                 105                 110

Asp Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
    130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Glu Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Gly Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Glu
            260                 265                 270

Phe Ile Gln Ile Gly Ser Asp Gly Gly Leu Leu Pro Arg Ser Val Lys
        275                 280                 285

```
-continued

Leu Thr Ser Phe Ser Leu Ala Pro Ala Glu Arg Tyr Asp Ile Ile Ile
    290                 295                 300

Asp Phe Thr Ala Tyr Glu Gly Gln Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
                340                 345                 350

Lys Tyr Leu Ala Ser Tyr Pro Ser Val Gln Asn Glu Arg Ile Gln Asn
            355                 360                 365

Ile Arg Thr Leu Lys Leu Ala Gly Thr Gln Asp Glu Tyr Gly Arg Pro
370                 375                 380

Val Leu Leu Leu Asn Asn Lys Arg Trp His Asp Pro Val Thr Glu Ala
385                 390                 395                 400

Pro Lys Ala Gly Thr Thr Glu Ile Trp Ser Ile Ile Asn Pro Thr Arg
                405                 410                 415

Gly Thr His Pro Ile His Leu His Leu Val Ser Phe Arg Val Ile Asp
            420                 425                 430

Arg Arg Pro Phe Asp Ile Ala His Tyr Gln Glu Ser Gly Ala Leu Ser
            435                 440                 445

Tyr Thr Gly Pro Ala Val Pro Pro Pro Ser Glu Lys Gly Trp Lys
    450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510

Lys Ser Asp Pro Asn Ser Ser Ser Val Asp Lys Leu His Arg Thr Arg
            515                 520                 525

Ala Pro Pro Pro Pro Leu Arg Ser Gly Cys
530                 535
```

METHOD FOR IMPROVING THE FERMENTABLE SUGAR YIELD FROM LIGNOCELLULOSIC

FIELD OF THE INVENTION

The invention relates to processes for the conversion of biomass into carbohydrates, notable fermentable sugars. It provides means and methods for increasing the yield of enzymatic digestion of a biomass, in particular in those cases where cellulose is converted into sugars using a cellulose converting enzyme.

BACKGROUND OF THE INVENTION

Cellulose and lignin from plants are among the most prominent renewable carbon sources. These molecules are comprised in plants as lignocellulose structures; fibers of cellulose polymers entangled in a network of lignin polymers. Lignocellulose is composed mainly of cellulose, hemicellulose and lignin. Lignin may make up to 25% of the lignocellulosic biomass. For fermentable sugar production, Miscanthus grass species, wood chips and the byproducts of lawn and tree maintenance are some of the more popular lignocellulosic materials. Corn stover, Panicum virgatum (switchgrass) and Miscanthus are the major biomass materials being studied today, due to their high productivity per acre. Cellulose, however, is contained in nearly every natural, free-growing plant, tree, and bush, in meadows, forests, and fields all over the world without agricultural effort or cost needed to make it grow.

The cellulose fraction of various lignocelluloses is a uniform structure consisting of β-1,4 linked glucose units. However, the biodegradability of cellulose may vary between plants, depending on the strength of association of the cellulose with other plant compounds. The composition and proportion of hemicellulose and lignin are highly dependent on the nature of the material. There is more lignin in softwoods (for example, spruce) than in hardwoods (for example, willow) or agricultural residues (for example, wheat straw or sugarcane bagasse), which makes softwood a particularly challenging material for ethanol production. The major hemicellulose component of hardwood and agricultural residues is xylan, while that of softwood is mostly mannan.

There are essentially two ways of producing ethanol from cellulose. First there are cellulolysis processes which consist of hydrolysis of sometimes pretreated lignocellulosic materials, using enzymes to break complex cellulose into simple sugars such as glucose, followed by fermentation and distillation. Second, there is also gasification that transforms the lignocellulosic raw material into gaseous carbon monoxide and hydrogen. These gases can then be converted to ethanol by fermentation or chemical catalysis.

The process involving cellulolysis can typically be divided into several stages: first, there may be a "pretreatment" phase, to make the lignocellulosic material such as wood or straw more amenable to hydrolysis. A hydrolysis (the actual cellulolysis) step, to break down the molecules into sugars followed by the separation of the sugar solution from the residual materials, notably lignin, followed by microbial fermentation of the sugar solution and distillation to produce roughly 95% pure alcohol.

Although lignocellulose is the most abundant plant material resource, its susceptibility has been curtailed by its rigid structure. As the result, an effective pretreatment is needed to liberate the cellulose from the lignin seal and its crystalline structure so as to render it accessible for a subsequent hydrolysis step. By far, most pretreatments are done through physical or chemical means.

Physical pretreatment is often called size reduction to reduce biomass physical size. Chemical pretreatment is to remove chemical barriers so the enzymes can have access to cellulose for enzymatic destruction.

To date, the available pretreatment techniques include acid hydrolysis, steam explosion, ammonia fiber expansion, organosolve, sulfite pretreatment to overcome recalcitrance of lignocellulose, alkaline wet oxidation and ozone pretreatment.

In acid-catalyzed pretreatment, the major part of the hemicellulose is degraded, and the cellulose has to be hydrolyzed by the use of cellulases, whereas in alkali-catalyzed pretreatment, part of the lignin is removed, and in addition to cellulases, hemicellulases are also needed to hydrolyze the remaining polysaccharides.

The complete hydrolysis of cellulose and hemicellulose requires a well-designed cocktail of enzymes consisting of endoglucanases, cellobiohydrolases, β-glucosidases, xylanases, mannanases and various enzymes acting on side chains of xylans and mannans.

Due to the recalcitrant structure of lignocelluloses, a pretreatment step may be required prior to enzymatic hydrolysis in order to make the cellulose more accessible to the enzymes. Despite of the above developments, most pretreatment processes are not effective when applied to feedstocks with high lignin content, such as forest biomass. The present invention addresses this problem.

SUMMARY OF THE INVENTION

We found that a Bacillus subtilis spore coat protein termed CotA could greatly improve the yield of the enzymatic digestion of lignocellulose material. The invention therewith relates to a method for producing a fermentable sugar from a lignocellulosic material wherein the lignocellulosic material is contacted with a laccase and an enzyme capable of degrading cellulose, either simultaneously or in a sequentially deferred fashion, wherein the laccase is the Bacillus spore coat protein CotA.

The invention also relates to an isolated nucleic acid encoding a protein useful in the above method, the protein having laccase activity and a primary amino acid sequence that is at least 93% identical with the sequence of COT1 (SEQ ID NO:1) or COT2 (SEQ ID NO:2). The invention also relates to an isolated polypeptide having laccase activity encoded by an isolated DNA sequence as described above or an isolated polypeptide having laccase activity with a primary amino acid sequence that is at least 93% identical with the sequence of COT1 (SEQ ID NO:1) or COT2 (SEQ ID NO:2).

DETAILED DESCRIPTION OF THE INVENTION

We surprisingly found that the yield of an enzymatic process for producing fermentable sugars from lignocellulosic material may greatly be improved when a Bacillus spore coat protein called CotA is added to the lignocellulosic material together or in a sequentially deferred fashion with an enzyme capable of degrading cellulose. In a series of experiments we were able to show that this CotA protein outperformed other laccases, both from bacterial and fungal origin.

Hence, the invention relates to a method for producing a fermentable sugar from a lignocellulosic material wherein the lignocellulosic material is incubated with a laccase and an enzyme capable of degrading cellulose, either simultaneously or in a sequentially deferred fashion, wherein the laccase is the *Bacillus* spore coat protein CotA.

Examples of a lignocellulosic material that may advantageously be treated with the methods of the invention include materials comprising corn stovers, bioenergy crops, agricultural residues, municipal solid waste, industrial solid waste, yard waste, wood and forestry waste, sugar cane, switchgrass, wheat straw, hay, barley, barley straw, rice straw, grasses, waste paper, sludge or byproducts from paper manufacture, corn grain, corn cobs, corn husks, grasses, wheat, wheat straw, hay, rice straw, sugar cane bagasse, sorghum, soy, trees, branches, wood chips, sawdust and any combination thereof.

The invention therefore relates to a method as described above wherein the lignocellulosic material is selected from the group consisting of corn stovers, bioenergy crops, agricultural residues, municipal solid waste, industrial solid waste, yard waste, wood and forestry waste, sugar cane, switchgrass, wheat straw, hay, barley, barley straw, rice straw, grasses, waste paper, sludge or byproducts from paper manufacture, corn grain, corn cobs, corn husks, grasses, wheat, wheat straw, hay, rice straw, sugar cane bagasse, sorghum, soy, trees, branches, wood chips, sawdust and any combination thereof.

The term lignocellulosic material refers to a material that comprises (1) cellulose, hemicellulose, or a combination and (2) lignin. Throughout this disclosure, it is understood that cellulose may refer to cellulose, hemicellulose, or a combination thereof. Cellulase may refer to cellulase, hemi-cellulase, or a combination thereof.

We also found that the action of a multitude of cellulose degrading enzymes could be improved. In a preferred embodiment, the invention relates to a method as described above, wherein the enzyme capable of degrading cellulose is selected from the group consisting of cellulase; hemi-cellulase; [beta] 1-4 endoglucanases (E.C. 3.2.1.4), [beta] 1-4 exoglucanases (E.C. 3.2.1.9.1), [beta]-glucosidases (E.C. 3.2.1.2.1), endoxylanase, and combinations thereof.

Cellulose-degrading enzymes are known in the art and commercially available. They are usually offered in combination preparations, for example, CELLIC CTEC3™ or CTEC2™ preparations (from Novozymes, Denmark) which are compositions of enzymes comprising cellulases, [beta]-glucosidases and hemi-cellulase; or CELLIC HTEC3™ or HTEC2™ (also from Novozymes, Denmark) which is a composition of enzymes comprising endoxylanase and cellulase.

In a preferred embodiment the CotA laccase is added to the lignocellulose material together with or before the cellulose-degrading enzyme.

In another preferred embodiment, the method may be employed to increase the yield of fermentable sugars obtained from a lignocellulose with a high content of lignin.

In certain processes, the temperature of the biomass or lignocellulosic material to be treated may be in excess of the enzyme inactivation temperature. Since a high temperature may inactivate enzymes by denaturing its amino acid chain, the enzyme may advantageously be added to the biomass at a point below the enzyme inactivation temperature. The enzymes may be added within the functional temperature range(s) or at the optimal temperature(s) of the enzyme. To save energy, the enzymes may be added after the biomass has cooled below the inactivation temperature and that the enzymatic process is completed sufficiently before the temperature has dropped below the optimal functional temperature of the enzyme. Naturally, it is also an option to maintain a desired temperature by cooling or heating the biomass or lignocellulosic material. Adding a dilution liquid, such as water at a certain temperature, may be used to cool the biomass.

In one embodiment, the enzyme pretreatment process may be performed at a specific temperature such as, for example at from 30 degrees C. to 60 degrees C.; 40 degrees C. to 55 degrees C.; or 45 degrees C. to 50 degrees C., or at room temperature or lower.

The contacting of the biomass with an enzyme can be performed for a period of time up to one day. While longer enzymatic digestions are possible, a shorter period of time such as 60 minutes, 10 hours, 20 hours, 30 hours, 40 hours, 60 hours or 72 hours or any time less than these values or any time between any of two of these values may be used for practical or economic reasons. In another preferred embodiment, the enzymatic digestions can take 50, 100, 150 or 200 hours or any time less than these values or any time between any of two of these values. See, e.g., the examples section. In one embodiment, a preferred period of enzyme contact is about 3 days or less.

In a method according to the invention, the lignocellulose material may advantageously be pretreated. The term "pretreated" as used herein refers to a treatment that occurs before the enzymatic treatment, either laccases or cellulose-degrading enzymes or both. Pretreatment may consist of a steam treatment, such as a dilute acid steam treatment or a steam explosion treatment is applied to the biomass or lignocellulose material. One of the goals of the steam treatment is to depolymerize the lignin in the biomass to a sufficient extent to allow an enzyme or mixture of enzymes to convert the cellulose and hemi-cellulose in the biomass into less complex sugars in a subsequent step.

Laccases (EC 1.10.3.2) are enzymes having a wide taxonomic distribution and belonging to the group of multicopper oxidases. Laccases are eco-friendly catalysts, which use molecular oxygen from air to oxidize various phenolic and non-phenolic lignin-related compounds as well as highly recalcitrant environmental pollutants, and produce water as the only side-product. These natural "green" catalysts are used for diverse industrial applications including the detoxification of industrial effluents, mostly from the paper and pulp, textile and petrochemical industries, use as bioremediation agent to clean up herbicides, pesticides and certain explosives in soil. Laccases are also used as cleaning agents for certain water purification systems. In addition, their capacity to remove xenobiotic substances and produce polymeric products makes them a useful tool for bioremediation purposes.

Laccases were originally discovered in fungi, they are particularly well studied in White-rot fungi and Brown-rot fungi. Later on, laccases were also found in plants and bacteria. Laccases have broad substrate specificity; though different laccases can have somewhat different substrate preferences. Main characteristic of laccase enzyme is its redox potential, and according to this parameter all laccases can be divided in three groups (see, for example, Morozova, O. V., Shumakovich, G. P., Gorbacheva, M. a., Shleev, S. V., & Yaropolov, a. I. (2007). "Blue" laccases. Biochemistry (Moscow), 72(10), 1136-1150. doi:10.1134/S0006297907100112): high redox potential laccases (0.7-0.8 V), medium redox potential laccases (0.4-0.7 V) and low redox potential laccases (<0.4V). It is believed that low redox potential limits the scope of substrates which the enzyme can possibly oxidize, and vice versa. All high redox potential laccases and the upper part of the medium redox potential laccases are fungal laccases. Industrial application of laccases is mostly if not entirely relying on fungal laccases.

CotA is a bacterial laccase and is a component of the outer coat layers of bacillus endospore. It is a 65-kDa protein encoded by the cotA gene (Martins, O., Soares, M., Pereira, M. M., Teixeira, M., Costa, T., Jones, G. H., & Henriques, A. O. (2002). Molecular and Biochemical Characterization of a Highly Stable Bacterial Laccase That Occurs as a Structural Component of the Bacillus subtilis Endospore Coat. Biochemistry, 277(21), 18849-18859. doi:10.1074/jbc.M200827200). CotA belongs to a diverse group of multi-copper "blue" oxidases that includes the laccases. This protein demonstrates high thermostability, and resistance to various hazardous elements in accordance with the survival abilities of the endospore. The redox-potential of this protein has been reported to be around 0.5 mV, which places it in the range of medium-redox-potential laccases.

In terms of primary structure, laccases are divers. In many cases laccases may have no significant sequence homology at all to other members of multi-copper oxidases.

CotA laccases represent a rather compact and well defined group of sequences. We performed Blast search of sequences from the Protein databank (blast.ncbi.nlm.nih.gov/Blast.cgi?PROGRAM=blastp&BLAST_PROGRAMS=blast p&PAGE_TYPE=BlastSearch&SHOW_DEFAULTS=on&LINK_LOC=blasthome) having homology to a preferred sequences of this patent application termed COT1 protein (SEQ ID NO: 1) and COT2 protein (SEQ ID NO: 2).

This search revealed a highly compact group of sequences showing between 98% and 91% identity to the COT2 sequence. Another group of sequences consisted exclusively of Bacillus species spore coat laccases, which had an identity between 78% and 82% to the COT1 sequence.

In the group of sequences with an identity of 60% or higher, all sequences were spore coat proteins from Bacillus species, products of corresponding CotA genes.

Alignment of COTA laccase, Gen Bank: BAA22774.1 with fungal Trametes versicolor laccase (GenBank: CAA77015) using "Blast 2 sequences" online resource (blast.ncbi.nlm.nih.gov/Blast.cgi?PAGE=Proteins&PROGRAM=blastp&BLAST ROGRAMS=blastp&PAGE_TYPE=BlastSearch&BLAST_SPEC=blast2seq) shows that only 54% of the sequence length could be aligned with an identity in the aligned section of 22%. Alignment of COT2 (SEQ ID NO: 2, a preferred CotA enzyme) to another bacterial laccase—CuEO from E. coli (ZP_03034325.1) showed 29% identity. So it can be said that CotA laccase has no significant identity or homology to other laccases.

For the purpose of this invention, CotA is defined herein as an isolated protein with laccase activity with a primary amino acid structure that is at least 60% identical to the sequence according to SEQ ID NO: 2. Preferably, CotA has a primary structure that is at least 60% identical to the sequence according to SEQ ID NO: 2, such as at least 65%, 70%, 75%, 80%, 85%, 90%, 91%, 92%, 93%, 94%, 95%, 96%, 97%, 98%, 99% or even 100%.

The invention also provides new and improved enzymes and methods for its use. Hence, the invention also relates to a method as described above wherein the CotA laccase has a primary amino acid structure that is at least 60% identical to the sequence of COT1 (SEQ ID NO:1) or COT2 (SEQ ID NO:2). In a further improvement of the invention, the CotA laccase is COT1 (SEQ ID NO:1) or COT2 (SEQ ID NO:2).

The invention also relates to an isolated nucleic acid encoding a protein having laccase activity and a primary amino acid sequence that is at least 93% identical with the sequence of COT1 (SEQ ID NO:1) or COT2 (SEQ ID NO:2).

The invention also relates to an isolated polypeptide having laccase activity encoded by an isolated DNA sequence as described above. In a particularly preferred embodiment, the invention relates to an isolated polypeptide having laccase activity with a primary amino acid sequence that is at least 60% identical with the sequence of COT1 (SEQ ID NO:1) or COT2 (SEQ ID NO:2).

LEGEND TO THE FIGURE

FIG. 1 Effect of laccases on reducing sugar yield from lignocellulosic biomass. Enzymatic hydrolysis of the lignocellulosic material (old corrugated cardboard) was performed using commercial cellulase cocktail for biofuel applications under recommended conditions, with or without laccases. Laccases were added (as indicated) at the concentration 1 ukat/g (60 units/g) of dry substrate, directly to the hydrolysis mixtures together with cellulases. Following laccases were used: "Fungal laccase 1" from Trametes versicolor, "fungal laccase 2" from Pleurotus ostreatus, and "CotA" spore coat protein from Bacillus subtilis. Reducing sugar yields were determined by DNS-method. Yield of the control reaction without laccase, ("cellulase") was taken as 100% and the relative yields for the corresponding samples containing laccases were calculated.

EXAMPLES

Example 1

Effect of Different Laccases on Sugar Yield from Enzymatic Hydrolysis of a Lignocellulosic Substrate Pieces of old corrugated cardboard were subjected to enzymatic hydrolysis. We carried out parallel experiments where hydrolysis of cellulose was performed in the absence of laccase or in the presence of one of the three laccases: (1) Spore coat protein from Bacillus subtilis CotA (COT2 SEQ ID NO:2, recombinantly expressed in E. coli), (2) commercially available fungal laccase from white-rot-fungi Trametes versicolor (available from Sigma-Aldrich), and (3) laccase from white-rot-fungi Pleurotus ostreatus recombinantly expressed in Yeast Saccharomyces cerevisiae (Piscitelli, A., Giardina, P., Mazzoni, C., & Sannia, G. (2005). Recombinant expression of Pleurotus ostreatus laccases in Kluyveromyces lactis and Saccharomyces cerevisiae. Applied microbiology and biotechnology, 69(4), 428-39. doi:10.1007/s00253-005-0004-z).

Pieces of old corrugated cardboard were pre-treated with 0.5% NaOH at 15% consistency (consistency means percentage of dry matter in the slurry, w/v) for 1 h at 90 degrees Celcius, then the material was washed with water, dried, and subjected to enzymatic hydrolysis at 5% consistency in 100 mM Succinic acid (pH 5.0).

Enzymatic hydrolysis of cellulose was carried out using commercially available cellulase cocktail for biofuel applications, CMAX (Alternafuel) from Diadick using manufacturer recommended concentration of cellulases.

All laccases were used at concentration 1 microkatal/g (60 units/g, of dry feedstock. One katal is defined as the amount of enzyme needed to convert 1 mole of substrate (ABTS) in 1 sec. A catalytic unit is defined as the amount of enzyme needed to convert 1 micromole of substrate (ABTS) in 1 min) and added directly to the hydrolysis reaction.

Hydrolysis was carried out at 60 degrees Celsius for 72 h. After the hydrolysis, reducing sugar levels were determined by Dinitrosalicylic Acid Method (DNS method, Sadasivam S., Manickam A., "Carbohydrates" in Biochemical methods, New Age Internatioal Ltd Publishers, 2nd edition, 2005, p. 6).

The results are shown in FIG. 1. We observed a large increase in yield when the lignocellulosic material was incubated simultaneously with CotA and the cellulase enzymes. An increase of approximately 250% was achieved in comparison to cellulases combined with white-rot-fungi *Trametes versicolor* or laccase from white-rot-fungi *Pleurotus ostreatus*. Very similar results were obtained when the laccase treatment was performed before the cellulase treatment.

Example 2

Enzymatic Hydrolysis of Various Lignocellulosic Feedstocks

Enzymatic hydrolysis of various lignocellulosic feedstocks was carried out in order to evaluate the effect of CotA laccase treatment on sugar yield (Table 1).

The following ligno-cellulosic substrates were used:

Steam exploded wheat straw: steam explosion was performed in a steam explosion instrument at 200 degrees Celsius for 2.5 min, the slurry after steam explosion was washed with water and dried. Old corrugated cardboard was treated with 0.5% NaOH at 15% consistency for 1 h at 90 degrees Celsius, then the material was washed with water and dried. *Eucalyptus* pulp is pulp (wood fibers) obtained by chemical pulping (kraft pulping) and collected after bleaching step. It is practically pure cellulose fibers with small traces of lignin. Blow pulp Soft wood (Spruce) and Blow pulp, Hard wood (birch) are pulps (wood fibers) obtained by chemical pulping (kraft pulping) collected before bleaching step from the Blow tank which drys pulp after chemical cooking. These pulps contain about 3% lignin and 97% cellulose. Pine pulp is pulp obtained from pine by thermomechanical pulping process, it was collected before bleaching and contains about 25% lignin and 75% cellulose.

Enzymatic hydrolysis of cellulose was carried out using commercially available cellulase cocktail for biofuel applications, CMAX (Alternafuel) from Diadick. Dried lignocellulosic substrates as described above were subjected to enzymatic hydrolysis at 5% consistency in 100 mM Succinic acid (pH 5.0) using manufacturer recommended concentration of cellulases. CotA laccase (where indicated) was added to the hydrolysis reactions at concentration 1 microkatal/g of dry feedstock (which corresponds to 60 units/g. One katal is defined as the amount of enzyme needed to convert 1 mole of substrate (ABTS) in 1 sec, catalytic unit is defined as the amount of enzyme needed to convert 1 micromole of substrate (ABTS) in 1 min). Hydrolysis was carried out at 60 degrees Celsius for 72 h.

After the hydrolysis, reducing sugar levels were determined by Dinitrosalicylic Acid Method (DNS method, Sadasivam, 2005). Results are shown in table 1.

It was concluded that the yields of the cellulase were greatly improved upon the addition of a CotA laccase to the reaction mixture, regardless of the source of the lignocellulose.

It was remarkably found that a biomass containing virtually no lignin or no lignin at all (such as *eucalyptus* pulp) could also serve as a substrate in a method according to the invention. Even with those materials, the yield of the cellulose was greatly improved when a CotA laccase was used in combination with the cellulase. As shown in table 1, the yield from *eucalyptus* pulp increased with 157% to a yield that was 92% of the theoretical yield.

TABLE 1

Improvement of sugar yield with CotA laccase.

| Lignocellulose material | Cellulase [mg sugar/ gram feedstock] | Cellulase + CotA Laccase [mg sugar/ gram feedstock] | Improvement of yield | Theoretical yield [mg sugar/gram feedstock] | Percentage of theoretical yield |
|---|---|---|---|---|---|
| Steam exploded wheat straw | 433 | 556 | 128% | 650 | 85% |
| Old Corrugated Cardboard (OCC) | 83 | 214 | 259% | 690 | 31% |
| Pine Pulp | 219 | 532 | 243% | 750 | 71% |
| Eucalyptus pulp | 586 | 922 | 157% | 1000 | 92% |
| Blow Pulp (Softwood) | 429 | 840 | 196% | 970 | 86% |
| Blow Pulp (Hardwood) | 542 | 950 | 175% | 970 | 98% |

The invention claimed is:

1. A method for producing a fermentable sugar from a lignocellulosic material, the method comprising:
   contacting the lignocellulosic material with a laccase and a mixture of cellulose-degrading enzymes,
   wherein the contacting is performed simultaneously or in a sequential fashion, and
   wherein the laccase is the *Bacillus* spore coat protein CotA;
   wherein the mixture of cellulose degrading enzymes comprises an exoglucanase; and
   wherein at least 31% of theoretical fermentable sugar yield is released from the lignocellulosic material.

2. The method according to claim 1, wherein the lignocellulosic material is selected from the group consisting of corn stovers, bioenergy crops, agricultural residues, municipal solid waste, industrial solid waste, yard waste, wood and forestry waste, sugar cane, switchgrass, wheat straw, hay, barley, barley straw, rice straw, grasses, waste paper, sludge or byproducts from paper manufacture, corn grain, corn cobs, corn husks, grasses, wheat, wheat straw, hay, rice straw, sugar cane bagasse, sorghum, soy, trees, branches, wood chips, sawdust and any combination thereof.

3. The method according to claim 1, wherein the cellulose-degrading enzymes of the mixture of cellulose-degrading enzymes are selected from the group consisting of cellulase, hemi-cellulase, [beta] 1-4 endoglucanases (E.C. 3.2.1.4), [beta] 1-4 exoglucanases (E.C. 3.2.1.9.1), [beta]-glucosidases (E.C. 3.2.1.2.1), and endoxylanase.

4. The method according to claim 1, wherein the lignocellulosic material is pretreated before the material is contacted with the laccase and the mixture of cellulose-degrading enzymes.

5. The method according to claim 4, wherein the pretreatment consists of a steam explosion step.

6. The method according to claim 1, wherein the CotA laccase has a primary amino acid structure having at least 60% sequence identity to the sequence of COT1 (SEQ ID NO:1) or COT2 (SEQ ID NO:2).

7. The method according to claim 6, wherein CotA is COT1 (SEQ ID NO:1) or COT2 (SEQ ID NO:2).

8. The method according to claim 2, wherein the cellulose-degrading enzymes of the mixture of cellulose-degrading enzymes are selected from the group consisting of cellulase, hemi-cellulase, [beta] 1-4 endoglucanases (E.C. 3.2.1.4), [beta] 1-4 exoglucanases (E.C. 3.2.1.9.1), [beta]-glucosidases (E.C. 3.2.1.2.1), and endoxylanase.

9. The method according to claim 2, wherein the lignocellulosic material is pretreated before the material is contacted with the laccase and the mixture of cellulose-degrading enzymes.

10. The method according to claim 3, wherein the lignocellulosic material is pretreated before the material is contacted with the laccase and the mixture of cellulose-degrading enzymes.

* * * * *